(12) United States Patent
Nakamura et al.

(10) Patent No.: US 8,082,773 B2
(45) Date of Patent: Dec. 27, 2011

(54) FUEL PROPERTY DETECTION DEVICE

(75) Inventors: Hiroshi Nakamura, Nishio (JP); Akikazu Uchida, Obu (JP); Daisuke Shikanai, Tokai (JP)

(73) Assignee: Denso Corporation, Kariya (JP)

( * ) Notice: Subject to any disclaimer, the term of this patent is extended or adjusted under 35 U.S.C. 154(b) by 163 days.

(21) Appl. No.: 12/720,279

(22) Filed: Mar. 9, 2010

(65) Prior Publication Data
US 2010/0229638 A1  Sep. 16, 2010

(30) Foreign Application Priority Data

Mar. 12, 2009  (JP) .................................. 2009-59385

(51) Int. Cl.
*G01M 15/09* (2006.01)

(52) U.S. Cl. .................................. 73/114.43; 73/114.55

(58) Field of Classification Search ............... 73/114.43, 73/114.55; 324/663, 698
See application file for complete search history.

(56) References Cited

U.S. PATENT DOCUMENTS

| | | | | |
|---|---|---|---|---|
| 4,939,467 A * | 7/1990 | Nogami et al. | ............... | 324/663 |
| 5,005,402 A * | 4/1991 | Pischinger et al. | ........... | 324/663 |
| 5,103,184 A * | 4/1992 | Kapsokavathis et al. | ..... | 324/672 |
| 5,196,801 A * | 3/1993 | Nogami et al. | ............... | 324/663 |
| 5,255,656 A * | 10/1993 | Rader et al. | .................... | 123/494 |
| 5,361,035 A * | 11/1994 | Meitzler et al. | ............... | 324/663 |
| 5,416,425 A * | 5/1995 | Mouaici | ........................ | 324/690 |
| 5,543,722 A * | 8/1996 | Suzuki et al. | ................. | 324/675 |
| 5,717,339 A * | 2/1998 | Murphy et al. | ............... | 324/693 |
| 6,927,583 B2 * | 8/2005 | Vanzuilen et al. | ............ | 324/686 |
| 7,030,629 B1 * | 4/2006 | Stahlmann et al. | ............ | 324/663 |
| 7,170,303 B2 * | 1/2007 | Vanzullen et al. | ............ | 324/690 |
| 7,466,147 B2 * | 12/2008 | Stahlmann | .................... | 324/663 |
| 7,800,379 B2 * | 9/2010 | Hernandez et al. | ........... | 324/663 |
| 2004/0004487 A1 * | 1/2004 | Vanzuilen et al. | ............ | 324/663 |

FOREIGN PATENT DOCUMENTS

| | | |
|---|---|---|
| JP | 1-163862 | 11/1989 |
| JP | 02-223854 | 9/1990 |
| JP | 04-350550 | 12/1992 |
| JP | 06-130019 | 5/1994 |
| JP | 06-249816 | 9/1994 |
| JP | 08-326622 | 12/1996 |
| JP | 2003-287513 | 10/2003 |

OTHER PUBLICATIONS

Japanese Office Action dated Dec. 16, 2010 issued in corresponding Japanese Application No. 2009-059385 with English Translation.

* cited by examiner

*Primary Examiner* — Freddie Kirkland, III
(74) *Attorney, Agent, or Firm* — Nixon & Vanderhye PC

(57) ABSTRACT

In a fuel property detection device, a fuel housing is made of a thin-plate metal member that can be elastically-deformed by a fuel pressure in a fuel chamber. Thus, if the fuel pressure in the fuel chamber is increased, the fuel housing expands and the pressure in the fuel chamber is decreased. Further, if the fuel pressure in the fuel chamber is decreased, the fuel housing contracts and the pressure in the fuel chamber is increased. That is, the fuel housing functions as a kind of damper. Therefore, in the fuel property detection device, generation of abnormal noise due to fuel pulsation or the like, and a positional change of the electrodes due to the fuel pulsation or the like can be prevented.

6 Claims, 4 Drawing Sheets

FUEL PROPERTY DETECTION DEVICE

CROSS REFERENCE TO RELATED APPLICATION

The present application is based on Japanese Patent Application No. 2009-59385 filed on Mar. 12, 2009, the disclosure of which is incorporated herein by reference.

FIELD OF THE INVENTION

The present invention relates to a fuel property detection device that detects a fuel property of a vehicle, for example.

BACKGROUND OF THE INVENTION

Low-pollution alcohol-blended gasoline receives attention as fuel of vehicles. An appropriate air-fuel ratio of such a blended gasoline is different from that of fuel including only gasoline. In order to control the air-fuel ratio of the blended gasoline to have an appropriate value, it is important to measure an alcohol content in the blended gasoline, that is, an alcohol concentration.

It is preferable that a physical constant having a relatively-high change ratio is used so as to measure the alcohol concentration with a high degree of accuracy. Conventionally, a method for detecting a change of a relative permittivity is disclosed. The relative permittivity can be obtained from a change of capacitance. For example, JP-U-1-163862 discloses a fuel sensor that measures the capacitance by using a pair of electrodes arranged to be opposed to each other.

However, in the above method, the pair of electrodes arranged to be opposed to each other has a cantilever structure, and thereby abnormal noise may be generated due to fuel pulsation or the like. The generation of the abnormal noise may bring a feeling of strangeness to a driver.

Further, if a relative positional relationship of the electrodes is changed due to the fuel pulsation, detection accuracy of the capacitance may be reduced.

Although the detection of the capacitance of alcohol-blended gasoline is described as an example, the above-described problem also may occur in the case of detecting a fuel property by using a pair of electrodes. An example of "the fuel property" includes capacitance or a relative permittivity that can be detected by the pair of electrodes.

SUMMARY OF THE INVENTION

In view of the above points, it is an object of the present invention to provide a fuel property detection device that can prevent abnormal noise generated due to fuel pulsation or the like, and a positional change of electrodes.

According to one aspect of the present invention, a fuel property detection device, which is arranged in a fuel pipe to detect a fuel property, the fuel property detection device includes a fuel housing defining a fuel chamber through which a fuel passes; an upstream pipe configured to supply the fuel into the fuel chamber, the upstream pipe being connected to an opening at an upstream side of the fuel housing; a downstream pipe configured to discharge the fuel from the fuel chamber, the downstream pipe being connected to an opening at a downstream side of the fuel housing; and at least a pair of electrodes arranged in the fuel chamber. The fuel housing is configured to be elastically-deformed by a pressure of the fuel in the fuel chamber.

Accordingly, the fuel housing is elastically-deformed by the fuel pressure in the fuel chamber. Thus, if the fuel pressure in the fuel chamber is increased, the fuel housing expands and the pressure in the fuel chamber is decreased. Further, if the fuel pressure in the fuel chamber is decreased, the fuel housing contracts and the pressure in the fuel chamber is increased. That is, the fuel housing functions as a kind of damper. Therefore, generation of abnormal noise due to fuel pulsation or the like can be prevented. Further, a positional change of the electrodes due to the fuel pulsation or the like can be prevented.

BRIEF DESCRIPTION OF THE DRAWING

The above and other objects, features and advantages of the present invention will become more apparent from the following detailed description made with reference to the accompanying drawing. In the drawing.

DETAILED DESCRIPTION OF THE PREFERRED EMBODIMENTS

Embodiment

Hereinafter, an embodiment of the present invention will be described with reference to the drawings.

A fuel property sensor of the present embodiment is arranged in a fuel pipe connecting a fuel tank to an injector of a vehicle, and measures an ethanol concentration in fuel.

Figure 1:
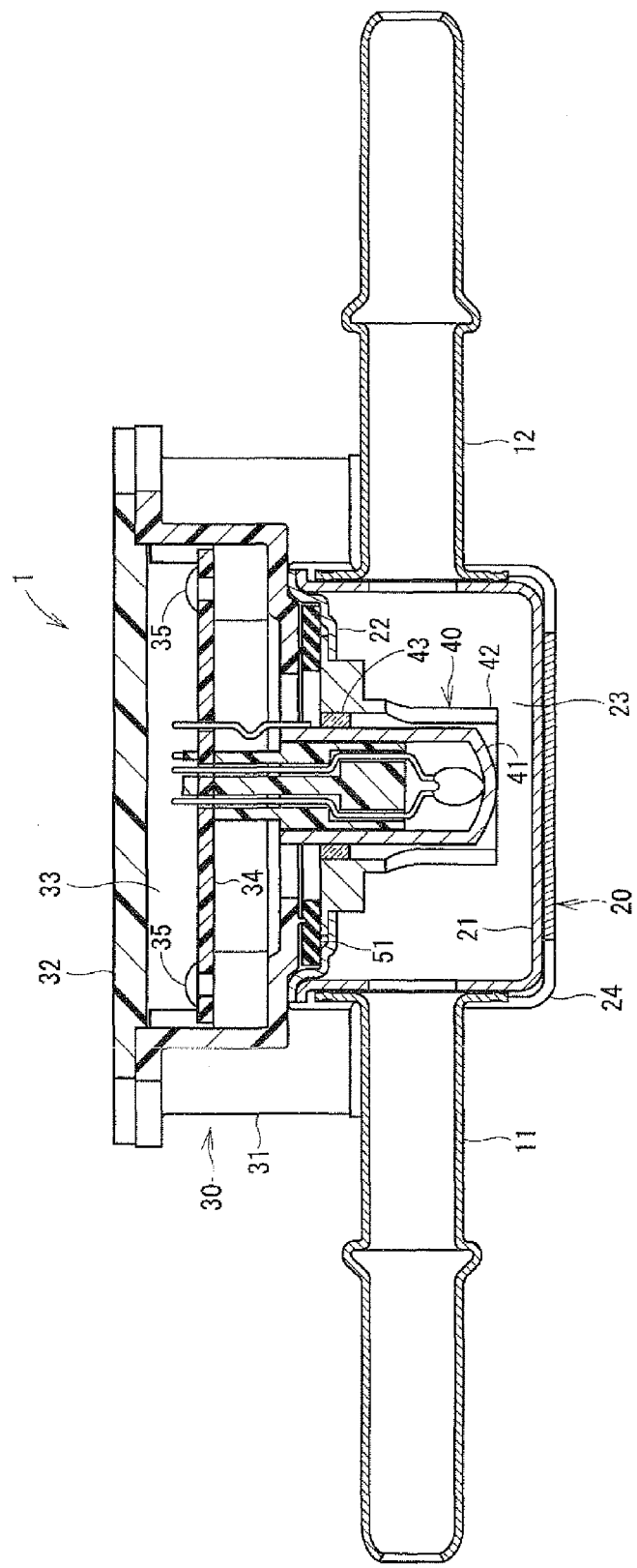
FIG. 1 is a schematic cross-sectional view showing a fuel property sensor according to an embodiment of the present invention.

As shown in FIG. 1, a fuel property sensor 1 includes an upstream pipe 11, a downstream pipe 12, which extend in a lateral direction in FIG. 1, a pipe configuration portion 20 arranged between the pipes 11, 12, a circuit configuration portion 30 arranged above the pipe configuration portion 20, and an electrode configuration portion 40 arranged inside the pipe configuration portion 20.

Figure 2:
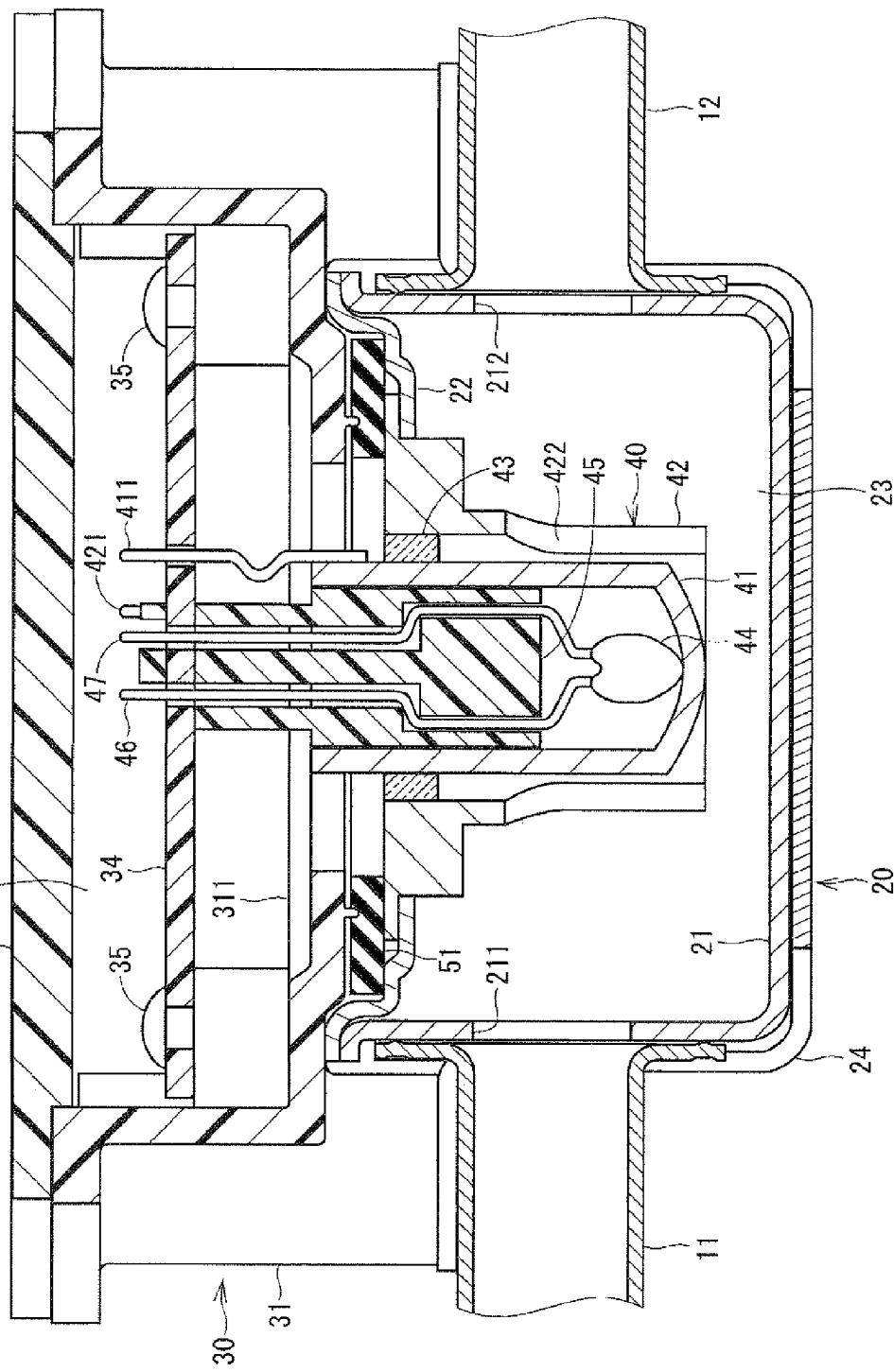
FIG. 2 is an enlarged schematic cross-sectional view showing the fuel property sensor according to the embodiment of the present invention.

The upstream pipe 11 is connected to a pipe at a side of the fuel tank. The downstream pipe 12 is connected to a pipe at a side of the injector. As shown in FIG. 2, the pipe configuring portion 20 is constructed mainly from a fuel housing 21. The fuel housing 21 is a container member made from metal (refer to FIG. 3), and has an opening at an upper portion thereof. A cover member 22 is attached to the opening at the upper portion, and the electrode configuration portion 40 is engaged with an opening at the center of the cover member 22 from above. Thus, a fuel chamber 23 is formed inside the fuel housing 21.

As shown in FIG. 2, a lower portion of the fuel housing 21 is covered by a bracket 24, and the fuel housing 21 has openings 211, 212 in a side wall thereof. The opening 211 is provided to be opposed to the upstream pipe 11, and thereby the fuel is supplied into the fuel chamber 23 from the upstream pipe 11. The opening 212 is provided to be opposed to the downstream pipe 12, and thereby the fuel is discharged from the fuel chamber 23 into the downstream pipe 12.

In particular, in the present embodiment, a flow passage area of the fuel chamber 23 is larger than a flow passage area of each of the upstream pipe 11 and the downstream pipe 12. Further, the fuel housing 21 is made of a thin-plate metal member that can be elastically-deformed by a fuel pressure in the fuel chamber 21

The circuit configuration portion 30 is constructed mainly from a hold housing 31 and a cover 32. The hold housing 31 and the cover 32 are made of resin material. The hold housing 31 has a concave portion 311. The cover 32 is arranged to cover an opening of the concave portion 311, thereby a hold chamber 33 is formed. A substrate 34 on which an electronic circuit is printed is housed in the hold chamber 33. The substrate 34 is fixed to the hold housing 31 by a screw 35.

The electrode configuration portion 40 includes a cylindrical first electrode 41 having a bottom and a cylindrical second electrode 42. The first electrode 41 is hermetically fixed to the second electrode 42 by a glass portion 43 (glass sealing) such that the first electrode 41 is located inside the second electrode 42 in a radial direction thereof. Thus, the first electrode 41 and the second electrode 42 are formed as one unit. The first and second electrodes 41, 42 are arranged to be opposed to each other.

Figure 3:
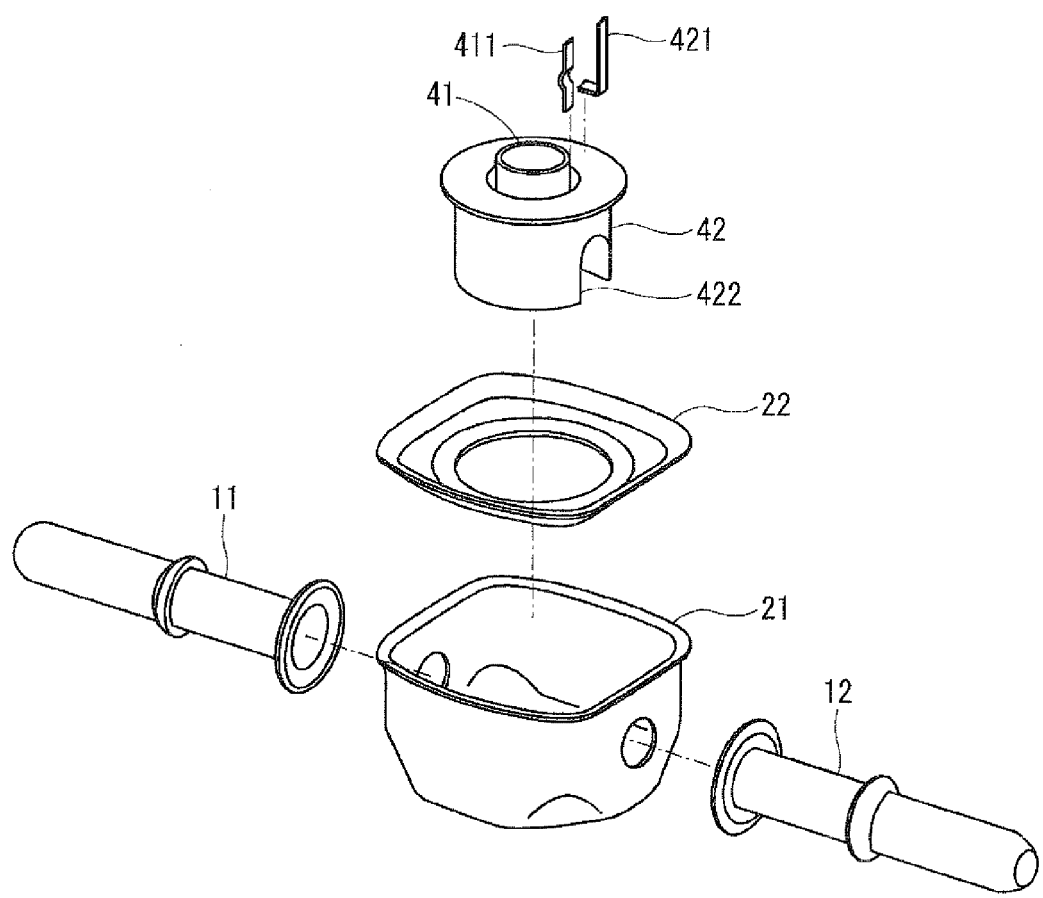
FIG. 3 is an exploded perspective view showing the fuel property sensor according to the embodiment of the present invention.

The first electrode 41 has a terminal 411 at a lateral side thereof. The terminal 411 is solder-mounted on the substrate 34. As shown in FIG. 3, the second electrode 42 has a terminal 421 on an upper surface thereof. The terminal 421 is solder-mounted on the substrate 34 as well as the terminal 411. Thus, a voltage value between the first electrode 41 and the second electrode 42 can be detected. Further, the second electrode 42 has a U-shaped cutout portion 422 at a side wall thereof. Thus, a space between the first electrode 41 and the second electrode 42 is filled with fuel flowing in the fuel chamber 23.

The first electrode 41 has a thermistor 44 therein. The thermistor 44 is supported by a resin supporting portion 45 that is fixed to the first electrode 41. Two terminals 46, 47 of the thermistor 44 penetrate the supporting portion 45, and are solder-mounted on the substrate 34. Thus, a fuel temperature can be detected via the first electrode 41.

Figure 4:
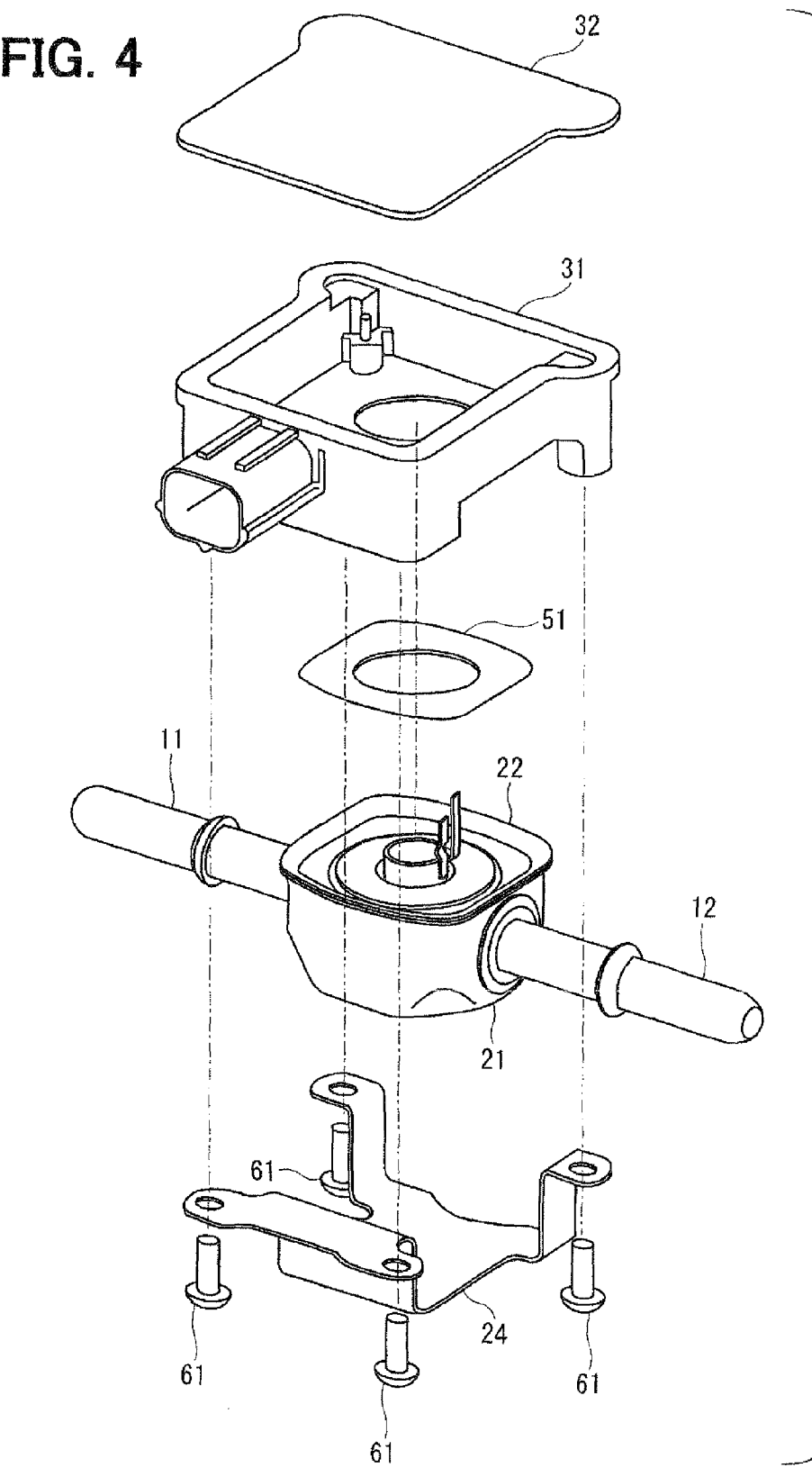
FIG. 4 is an exploded perspective view showing the fuel property sensor according to the embodiment of the present invention.

As shown in FIG. 4, the circuit configuration portion 30 is fitted to the pipe configuration portion 20 via an elastic member 51. The elastic member 51 is made of elastomer material and has a circular opening at the center portion thereof. Thus, the elastic member 51 is sandwiched between a peripheral portion of the second electrode 42 and a bottom portion of the hold housing 31 in the fitting of the circuit configuration portion 30 to the pipe configuration portion 20. Specifically, as shown in FIG. 4, the bracket 24 is fixed to the hold housing 31 by a screw 61 with the electrode configuration portion 40 engaged with the cover member 22, and thereby the hold housing 31 is fitted to the fuel housing 21. In FIG. 4, the substrate 34 or the like is not shown.

Accordingly, in the fuel property sensor 1 of the present embodiment, capacitance corresponding to a relative permittivity of the fuel passing through the fuel chamber 23 is detected, and the capacitance is corrected by the fuel temperature detected by the thermistor 44, thereby the ethanol concentration in the fuel is measured.

In the embodiment described in detail, the fuel housing 21 is made of the thin-plate metal member that can be elastically-deformed by the fuel pressure in the fuel chamber 23. Thus, if the fuel pressure in the fuel chamber 23 is increased, the fuel housing 21 expands and the pressure in the fuel chamber 23 is decreased. Further, if the fuel pressure in the fuel chamber 23 is decreased, the fuel housing 21 contracts and the pressure in the fuel chamber 23 is increased. That is, the fuel housing 21 functions as a kind of damper. Therefore, generation of the abnormal noise due to fuel pulsation or the like can be prevented. Further, a relative positional change of the electrodes 41, 42 due to the fuel pulsation or the like can be prevented.

In the present embodiment, the flow passage area of the fuel chamber 23 is larger than the flow passage area of each of the upstream pipe 11 and the downstream pipe 12. Therefore, the pressure loss of the fuel in the fuel chamber 23 can be suppressed.

In the present embodiment, the first electrode 41 is hermetically fixed to the second electrode 42 by the glass portion 43 (glass sealing) such that the first electrode 41 is located inside the second electrode 42 in the radial direction thereof. Thus, the first electrode 41 and the second electrode 42 are formed as one unit. Therefore, a fixing process can be simplified.

In the present embodiment, the first electrode 41 has the thermistor 44 therein. Thus, the fuel temperature can be detected, and measurement accuracy of the ethanol concentration can be increased.

It is to be noted that the fuel property sensor 1 corresponds to "a fuel property detection device", the fuel chamber 23 corresponds to "a fuel chamber", the fuel housing 21 corresponds to "a fuel housing", the upstream pipe 11 corresponds to "an upstream pipe", the downstream pipe 12 corresponds to "a downstream pipe", the first electrode 41 and the second electrode 42 correspond to "a pair of electrodes", the first electrode 41 corresponds to "a first electrode", the second electrode 42 corresponds to "a second electrode", and the thermistor 44 corresponds to "a temperature detection portion" in the present embodiment.

The present invention is not limited to the above-described embodiment, and can be modified in various ways without departing from the scope of the invention.

For example, the fuel housing 21 is made of metal material in the above-described embodiment. However, the material of the fuel housing 21 is not limited thereto as long as the fuel housing 21 functions as a damper.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A fuel property detection device, which is arranged in a fuel pipe to detect a fuel property, the fuel property detection device comprising:
   a fuel housing defining a fuel chamber through which a fuel passes;
   an upstream pipe configured to supply the fuel into the fuel chamber, the upstream pipe being connected to an opening at an upstream side of the fuel housing;
   a downstream pipe configured to discharge the fuel from the fuel chamber, the downstream pipe being connected to an opening at a downstream side of the fuel housing; and
   at least a pair of electrodes arranged in the fuel chamber, wherein
   the fuel housing is configured to be elastically-deformed by a pressure of the fuel in the fuel chamber.

2. The fuel property detection device according to claim 1, wherein
   the fuel housing is made of a thin-plate member.

3. The fuel property detection device according to claim 2, wherein the thin-plate member includes metal.

4. The fuel property detection device according to claim 1, wherein
the fuel housing is configured such that a flow passage area of the fuel chamber is larger than a flow passage area of each of the upstream pipe and the downstream pipe.

5. The fuel property detection device according to claim 1, wherein
the pair of electrodes includes a first electrode and a second electrode,
the second electrode is arranged around the first electrode and is opposed to the first electrode, and
the first electrode is fixed to the second electrode by glass sealing.

6. The fuel property detection device according to claim 5, wherein
the first electrode has a cylindrical shape with a bottom,
the first electrode has therein a temperature detection portion configured to detect a temperature of the fuel via the first electrode.

* * * * *